United States Patent [19]
Pamukcu et al.

[11] Patent Number: 5,643,959
[45] Date of Patent: Jul. 1, 1997

[54] METHOD FOR TREATING PATIENTS WITH PRECANCEROUS LESIONS BY ADMINISTERING SUBSTITUTED SULFONYL INDENYL ACETIC AND PROPIONIC ACIDS AND ESTERS THEREOF

[75] Inventors: Rifat Pamukcu, Cincinnati, Ohio; Klaus Brendel, Tucson, Ariz.

[73] Assignees: Cell Pathways, Inc., Aurora, Colo.; University of Arizona, Tucson, Ariz.

[21] Appl. No.: 361,291

[22] Filed: Dec. 22, 1994

Related U.S. Application Data

[63] Continuation of Ser. No. 839,203, Feb. 20, 1992, Pat. No. 5,401,774, which is a continuation-in-part of Ser. No. 666,796, Mar. 8, 1991, abandoned.

[51] Int. Cl.⁶ .................................................. A61K 31/19
[52] U.S. Cl. .................................................. 514/569
[58] Field of Search ....................................... 514/569

[56] References Cited

U.S. PATENT DOCUMENTS

| | | | |
|---|---|---|---|
| 3,161,654 | 12/1964 | Shen ....................... | 455/35.1 |
| 3,647,858 | 3/1972 | Hinkley et al. ........... | 566/11 |
| 3,654,349 | 4/1972 | Shen et al. ............... | 562/428 |
| 4,423,075 | 12/1983 | Dvornik et al. .......... | 514/569 |

OTHER PUBLICATIONS

Waddell, W.R. et al., Am. J. Surgery, vol. 157, pp. 175-179 (1989).
Gonzaga, R.A.F. et al., The Lancet, Mar. 30, 1985, p. 751.
Waddell, W.R. et al., J. Surg. Oncology, vol. 24, pp. 83-87 (1983).
Federation Proceedings (1972) of the Federation of American Societies for Experimental Biology abstract Nos. 2044 and 2045.
Gilman, S.C. et al., Nonsteroidal Anti-inflammatory Drugs in Cancer Therapy, (CIRCA 1985).
Brogden, R.N. et al., Drugs, vol. 16, pp. 97-114 (1978).
Hucker, H.B. et al., Drug Metabolism & Disposition, vol. 1, No. 6, pp. 721-736 (1973).
Shen, T.Y. et al., Chemical and Biological Studies on Indomethacin, Sulindac and Their Analogs, pp. 107-178 (circa 1975).
Duggan, D.E. et al., Clin. Pharm. & Therapeutics, vol. 21, No. 3, pp. 326-335 (1976).
Duggan, D.E. et al., J. Pharm. & Exper. Therap., vol. 201, No. 1, pp. 8-13 (1977).
Glavin, G.B. et al., Toxicology and Applied Pharmacology, vol. 83, pp. 386-389 (1986).
Moorghen, M. et al., Journal of Pathology, vol. 156, pp. 341-347 (1988).
Moorghen, M. et al., Acta Histochemica, Suppl.-Band XXIX, S. 195-199 (1990).
Bjarnason et al., Gastroenterology, vol. 94, No. 4, pp. 1070-1074 (1988).

*Primary Examiner*—John W. Rollins
*Attorney, Agent, or Firm*—Brinks Hofer Gilson & Lione

[57] ABSTRACT

Substituted indenyl sulfonyl acetic acids are useful to inhibit growth of precancerous lesions.

11 Claims, No Drawings

METHOD FOR TREATING PATIENTS WITH PRECANCEROUS LESIONS BY ADMINISTERING SUBSTITUTED SULFONYL INDENYL ACETIC AND PROPIONIC ACIDS AND ESTERS THEREOF

This is continuation of U.S. patent application Ser. No. 07/839,203, filed Feb. 20, 1992, now U.S. Pat. No. 5,401,774 which is a continuation-in-part of U.S. patent application Ser. No. 07/666,796 filed Mar. 8, 1991 now abandoned.

TECHNICAL FIELD

This invention relates to methods for treatment or prevention of precancerous lesions.

BACKGROUND OF THE INVENTION

Each year in the United States alone, untold numbers of people develop precancerous lesions. These lesions exhibit the strong tendency to develop into carcinomas. Such lesions include lesions of the breast (that can develop into breast cancer), lesions of the skin (that can develop into malignant melanoma) and colonic polyps (that can develop into colon cancer).

For example, approximately 60,000 people die from colon cancer, and over 150,000 new cases of colon cancer are diagnosed. For the American population as a whole, individuals have a six percent lifetime risk of developing colon cancer, making it the second most prevalent form of cancer in the country. Colon cancer is also prevalent in Western Europe.

To date, little progress has been made in the prevention and treatment of colorectal cancer, as reflected by the lack of change in the five-year survival rate over the last few decades. The only cure for this cancer is surgery at an extremely early stage. Unfortunately, most of these cancers are discovered too late for surgical cure, because most victims do not experience symptoms until the disease is advanced.

The incidence of colon cancer increases with age, particularly after the age of 40. Since the mean ages of populations in America and Western Europe are increasing, the prevalence of colorectal cancer should increase in the future.

In view of these grim statistics, efforts in recent years have concentrated on colon cancer prevention. Colon cancer usually arises from pre-existing benign growths known as polyps. Prevention efforts have emphasized the identification and removal of colonic polyps. Polyps are identified by x-ray and/or colonoscopy, and usually removed by devices associated with the colonoscope. The increased use of colon x-rays and colonoscopies in recent years has detected clinically significant precancerous polyps in four to six times the number of individuals per year that acquire colon cancer. During the past five years alone, an estimated 3.5 to 5.5 million people in the United States have been diagnosed with adenomatous colonic polyps, and it is estimated that many more people have or are susceptible to developing this condition, but are as yet undiagnosed. In fact, there are estimates that 10–12 percent of people over the age of 40 will form clinically significant adenomatous polyps.

Removal of polyps has been accomplished either with surgery or fiber-optic endoscopic polypectomy—procedures that are uncomfortable, costly (the cost of a single polypectomy ranges between $1,000 and $1,500 for endoscopic treatment and more for surgery), and involve a small but significant risk of colon perforation. Overall, about $2.5 billion is spent annually in the United States in colon cancer treatment and prevention.

As indicated above, each polyp carries with it a chance that it will develop into a cancer. The likelihood of cancer is diminished if a polyp is removed. However, many of these patients demonstrate a propensity for developing additional polyps in the future. They must, therefore, be monitored periodically for the rest of their lives for polyp reoccurrence.

In most cases (i.e. the cases of so-called common sporadic polyps), polyp removal will be effective to reduce the risk of cancer. In a small percentage of cases (i.e. the cases of the so-called polyposis syndromes), removal of all or part of the colon is indicated. The difference between common sporadic polyps and polyposis syndromes is dramatic. Common sporadic polyp cases are characterized by relatively few polyps, each of which can usually be removed leaving the colon intact. By contrast, polyposis syndrome cases can be characterized by many (e.g. hundreds or more) of polyps—literally covering the colon in some cases—making safe removal of the polyps impossible short of surgical removal of the colon. Because each polyp carries with it the palpable risk of cancerous development, polyposis syndrome patients invariably develop cancer if left untreated. Many of these patients have undergone a severe change in lifestyle as a result of the disfiguring surgery. Patients have strict dietary restrictions, and many must wear ostomy appliances to collect their intestinal wastes.

Recently, several non-steroidal anti-inflammatory drugs ("NSAIDs"), originally developed to treat arthritis, have shown effectiveness in inhibiting and eliminating polyps. Polyps virtually disappear when the patient take the drug, particularly when the NSAID sulindac is administered. However, the prophylactic use of currently available NSAIDs, even in polyposis syndrome patients, is marked by severe side reactions that include gastrointestinal irritations and ulcerations. Once NSAID treatment is terminated due to such complications, the polyps return, particularly in polyposis syndrome patients.

Sulindac has been particularly well received among the NSAIDs for polyp treatment. Sulindac is a sulfoxide compound that itself is believed to be inactive an anti-arthritic agent. The sulfoxide is reported to be converted by liver enzymes to the corresponding sulfide, which is acknowledged to be the active moiety as a prostaglandin inhibitor. The sulfide, however, is associated with the side effects of conventional NSAIDs. The sulfoxide is also known to be metabolized to a sulfone compound, which is regarded to be inactive as an inhibitor of prostaglandin synthesis.

SUMMARY OF THE INVENTION

This invention is a method of treating patients with precancerous lesions by administering a physiologically effective amount of a compound of formula I below to a patient in need of such treatment. Such compositions are effective in eliminating and inhibiting precancerous lesions, but are not characterized by the severe side reactions of conventional NSAIDs.

The compounds used in the treatment of this invention are believed to be effective on precancerous lesions either because they are active themselves or because they are metabolized to active derivatives.

It was unexpectedly discovered that while the sulfone compounds of this invention do not greatly inhibit prostaglandin synthesis—prostaglandin synthesis inhibition being a characteristic of conventional NSAIDs—the compounds of this invention nonetheless have antiproliferative effects on the cells of a precancerous lesion or precancerous cells.

DETAILED DESCRIPTION OF THE INVENTION

As discussed above, the present invention is a method of treating a patient with precancerous lesions by administering a physiologically effective amount of a compound of formula I below:

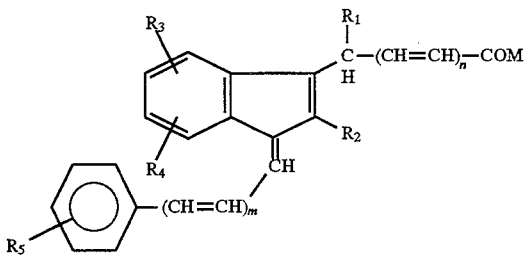

wherein $R_1$ is selected from the group consisting of hydrogen, lower alkyl, or haloalkyl;

$R_2$ is selected from the group consisting of hydrogen or alkyl;

$R_3$ and $R_4$ are one or more members each independently chosen from the group consisting of hydrogen, alkyl, acyloxy, alkoxy, nitro, amino, acylamino, alkylamino, diakylamino, dialkylaminoalkyl, sulfamyl, alkythio, mercapto, hydroxy, hydroxyalkyl, alkylsulfonyl, halogen, cyano, carboxyl, carbalkoxy, carbamido, haloalkyl, or cycloalkoxy;

$R_5$ is alkylsulfonyl;

m is 0 or 1;

n is 0 or 1; and

M is selected from the group consisting of hydroxy, substituted lower alkoxy, amino, alkylamino, dialkylamino, N-morpholino, hydroxyalkylamino, polyhydroxyamino, dialkylaminoalkylamino, aminoalklyamino, and the group OMe, wherein Me is a cation.

Preferably, the aforesaid method involves the administration of compounds of formula I wherein m and n are zero, i.e., compounds of formula II below wherein $R_1$–$R_5$, and M are as defined above:

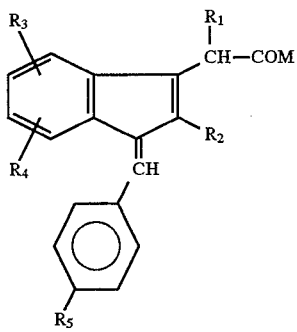

As used herein, the term "precancerous lesion" refers to lesions that exhibit histologic changes which are associated with an increased risk of cancer development. Examples include adenomatous polyps of the colon, dysplastic nevi of the skin and atypical hyperplasia of the breasts. Certain syndromes that commonly display precancerous lesions are also referred to by the term "precancerous" including dysplastic nevus syndrome and the colonic polyposis syndromes. "Precancerous" refers to these lesions or syndromes of various tissues whether or not the lesions are clinically identifiable.

As used herein, the term "halo" or "halogen" refers to chloro, bromo, fluoro and iodo groups, and the term "alkyl" refers to straight, branched or cyclic alkyl groups.

The present invention is also a method of treating individuals with precancerous lesions by administering a pharmaceutically effective amount of an enterically coated compounds of formulae I or II above where $R_1$–$R_5$ are as defined above.

Compounds of formulae I or II may be formulated into compositions together with pharmaceutically acceptable carriers for oral administration in solid or liquid form, or for rectal administration, although carriers for oral administration are most preferred.

Pharmaceutically acceptable carriers for oral administration include capsules, tablets, pills, powders, troches and granules. In such solid dosage forms, the carrier can comprise at least one inert diluent such as sucrose, lactose or starch. Such carriers can also comprise, as is normal practice, additional substances other than diluents, e.g., lubricating agents such as magnesium stearate. In the case of capsules, tablets, troches and pills, the carriers may also comprise buffering agents. Carriers such as tablets, pills and granules can be prepared with enteric coatings on the surfaces of the tablets, pills or granules. Alternatively, the enterically coated compound can be pressed into a tablet, pill, or granule, and the tablet, pill or granules for administration to the patient. Preferred enteric coatings include those that dissolve or disintegrate at colonic pH such as shellac or Eudraget S.

Pharmaceutically acceptable carriers include liquid dosage forms for oral administration, e.g. pharmaceutically acceptable emulsions, solutions, suspensions, syrups and elixirs containing inert diluents commonly used in the art, such as water. Besides such inert diluents, compositions can also include adjuvants such as wetting agents, emulsifying and suspending agents, and sweetening, flavoring and perfuming agents.

Pharmaceutically acceptable carriers for rectal administration are preferably suppositories which may contain, in addition to the compounds of Formulae I or II, excipients such as cocoa butter or a suppository wax.

The pharmaceutically acceptable carrier and compound of Formulae I or II are formulated into unit dosage forms for administration to a patient. The dosage levels of active ingredient (i.e. compounds of Formulae I or II) in the unit dosage may be varied so as to obtain an amount of active ingredient effective to achieve polyp-eliminating activity in accordance with the desired method of administration (i.e oral or rectal). The selected dosage level therefore depends upon the nature of the active compound administered, the route of administration, the desired duration of treatment, and other factors. If desired, the unit dosage may be such that the daily requirement for active compound is in one dose, or divided among multiple doses for administration, e.g. two to four times per day.

The foregoing may be better understood from the following examples, which are presented for purposes of illustration and are not intended to limit the scope of the invention. As used in the following examples, the references to substituents such as R, $R_1$, $R_2$ etc., refer to the corresponding compounds and substituents in the Formulae above.

Example 1

5-Methoxy-2-Methyl-1-(p-Methylsulfonylbenzylidene)-3-Indenyl Acetic Acid (A) α-Methyl-β-(p-methylthiophenyl) propionic acid.

To a solution of 2.3 g. (0.1 mole) of sodium in 100 ml. of absolute alcohol is added 17.4 g. (0.1 mole) of diethyl methylmalonate and 17.3 g. (0.1 mole) of p-methylthiobenzylchloride. The mixture is heated under a reflux in a water bath for three hours. The reaction mixture is poured into water, and the aqueous solution is extracted six times with ether and dried. It is then evaporated to yield diethyl methyl-p-methylthiobenzyl malonate. The crude product is then saponified by heating with excess 4% sodium hydroxide in aqueous ethanolic solution. The solution thus formed is concentrated, extracted with ether to remove any neutral material, and acidified with dilute sulfuric acid. The acidic mixture is heated on a steam bath for one hour, cooled and then extracted with ether. Evaporation of the ether solution gives α-methyl-β-(p-methylthiophenyl) propionic acid.

In a similar manner, using other substituted malonic esters in place of diethyl methylmalonate and other substituted benzyl halides in place of p-methylthiobenzyl chloride, the corresponding substituted propionic acids are obtained, for example:

α-methyl-β-(p-methoxyphenyl)propionic acid,

α-allyl-β-(p-nitrophenyl)propionic acid.

(B) 6-methoxy-2-methylindanone

α-Methyl-β-(p-methoxyphenyl)propionic acid (15 g.) is added to polyphosphoric acid (170 g.) at 50° C. and the mixture is heated at 83°–90° for two hours. The syrup is poured into iced water, stirred for one-half hour, and then extracted with ether three times. The ether solution is washed with water twice, and with 5% NaHCO$_3$ five times until all the acidic material has been removed. The remaining neutral solution is washed with water and dried over sodium sulfate. Evaporation of the solution gives the indanone as a pale yellow oil.

In a similar manner, other β-aryl propionic acid compounds are converted to the corresponding indanone by the procedure of this example.

(C) Methyl 5-methoxy-2-methyl-3-indenylacetate.

A solution of 13.4 g. of 6-methoxy-2-methylindanone and 19.3 g. of methyl bromoacetate in 45 ml. benzene is added over a period of 5 minutes to 21 g. of zinc amalgam (prepared according to Org. Syn. Coll., vol. 3) in 110 ml. benzene and 40 ml. dry ether. A few crystals of iodine are added to start the reaction, and the reaction mixture is maintained at reflux temperature (ca. 65°) with external heating. At three hour intervals, two batches of 10 g. zinc amalgam and 10 g. bromoester are added, and the mixture is then refluxed for eight hours. After addition of 30 ml. ethanol and 150 ml. of acetic acid, the mixture is poured into 700 ml. of 1:1 aqueous acetic acid. The organic layer is separated, and the aqueous layer is extracted twice with ether. The combined organic layers are washed thoroughly with water, ammonium hydroxide and water. Drying over sodium sulfate, evaporation of solvent in vacuo followed by pumping at 80° (bath temp.) (1–2 mm.) gives crude methyl (1-hydroxy-2-methyl-6-methoxy-indenyl)acetate.

A mixture of the above crude hydroxyester, 20 g. of p-toluenesulfonic acid monohydrate and 20 g. of anhydrous calcium chloride in 250 ml. toluene is refluxed overnight. The solution is filtered, and the solid residue is washed with benzene. The combined benzene solution is washed with water, sodium bicarbonate, water and then dried over sodium sulfate. After evaporation, the crude methyl 5-methoxy-2-methyl-3-indenylacetate is chromatographed on acid-washed alumina, and the product is eluted with petroleum ether-ether (v./v. 50–100%).

Methyl 2,6-Dimethyl-3-Indenylacetate

The above reactions of Example 1C are repeated except that the starting materials are 2,5-dimethylindanone and methylbromoacetate. With the same reaction conditions and techniques, methyl 2,6-dimethyl-3-indenylacetate is obtained.

The above reactions of Example 1C are repeated except that the starting materials are 6-methylthioindanone and methylbromoacetate. Using the same reaction conditions and techniques, there is obtained methyl 5-methyl-thio-2-methyl-3-indenylacetate.

When any of the other indanones described in the other examples of the specification are used in the above procedure in place of 6-methoxy-2-methylindanone the corresponding methyl ester is obtained.

(D) 5-methoxy-2-methyl-1-(p-methylthiobenzylidene)-3-indenyl acetic acid.

To a solution of methyl 5-methoxy-2-methyl-3-indenylacetate 8.7 g. (0.037 mole) and p-methylthiobenzaldehyde, 6.3 g. (1.1 equivalent) is added 16+ ml. (2.0+ equivalents) of 25% methanolic sodium methoxide. The mixture is stirred at reflux under nitrogen for 2 hours. An equal volume of water is added dropwise and refluxing continues for 30 min. The solution is cooled, diluted with water and extracted with ether (3×). Residual ether is blown off with nitrogen, and then the aqueous solution is acidified with 50% glacial acetic acid. The precipitated product is collected and washed thoroughly with water. The crude product is crystallized from methanol to give pure 5-methoxy-2-methyl-1-(p-methylthiobenzylidene)-3-indenyl acetic acid (M.P. 195°–196°).

5-Methoxy-2-Methyl-1-(p-Ethylthiobenzylidene)-3-Indenyl Acetic Acid.

The above reaction of Example 1D is repeated using p-ethylthiobenzaldehyde instead of p-methylthiobenzaldehyde. Using the same reaction conditions and techniques, there is obtained 5-methoxy-2-methyl-1-(p-ethylthiobenzylidene)-3-indenyl acetic acid.

5-Hydroxy-2-Methyl-1-(p-Methylthiobenzylidene)-3-Indenyl Acetic Acid

The reaction of Example 1D is repeated except that the starting materials are methyl 5-hydroxy-2-methyl-3-indenylacetate and p-methylthiobenzaldehyde. Using the same reaction conditions and techniques, there is obtained 5-hydroxy-2-methyl-1-(p-methylthiobenzylidene)-3-indenyl acetic acid.

The other methyl esters of Example 1C are reacted with p-methylthiobenzaldehyde according to the above procedure to produce the corresponding indenyl acetic acid.

(E) 5-methoxy-2-methyl-1-(p-methylsulfonylbenzylidene)-3-indenyl acetic acid.

A solution of sodium periodate (0.214 g.; 0.001 mole) in 3 ml. of water is added dropwise to 5-methoxy-2-methyl-1-(p-methylthiobenzylidene)-3-indenyl acetic acid (0.352 g.) (0.001 mole) in 25 ml. methanol and enough acetone to cause solution. This solution is stirred overnight at room temperature and filtered. The filtrate is evaporated at 30° to a sufficiently small volume that causes the product to precipitate. The suspension is diluted with several volumes of water, cooled and collected. The product is dried in vacuo over potassium hydroxide pellets and then in a vacuum oven at 70° to give 5-methoxy-2-methyl-1-(p-methylsulfinylbenzylidene)-3-indenyl acetic acid (M.P. 200.5°–203.5°).

5-methoxy-2-methyl-1-(p-methylsulfonylbenzylidene)-3-indenyl acetic acid is prepared by the dissolving 0.03 moles of the sulfoxide in 25 ml. methanol, and 50 ml.

acetonitrile are added. The solution is stirred at 0 C., and 0.03 moles of sodium methoxide are added dropwise. Stirring is continued, and 0.06 mole sodium bicarbonate is added as well a 0.06 moles of $H_2O_2$ (30% solution in water). The temperature is then dropped to −10 C., and stirring continued for 30 hours. At this time the $NaHCO_3$ is filtered and washed on the filter with a few ml. of cold methanol. The washings are returned to the filtrate and the $NaHCO_3$ is discarded. The filtrate is neutralized with 0.07 moles of HCl (concentrated HCl), partially evaporated to 50% of the original volume, and returned to the freezer for crystallization. Crystals of the sulfone derivative are collected. Additional sulfone can be collected from the mother liquor in a similar manner. ($R_1$=hydrogen; $R_2$=$CH_3$; $R_3$=5—$OCH_3$; $R_4$=hydrogen; $R_5$=p—$CH_3SO_2$)

Similarly, 5-methoxy-2-methyl-1-(ρ-ethylsulfonylbenzylidene)-3-indenyl acetic acid and 5-hydroxy-2-methyl-1-(ρ-methylsulfonylbenzylidene)-3-indenyl acetic acid be produced following the reaction of Example 1E using the compounds from Example 1D.

Example 2

5-Methoxy-2-Methyl-1-(ρ-Methylsulfonylbenzylidene)-3-Indenyl Acetic Acid (A) 6-methoxy-2-methylindanone.

In a 500 ml. 3-necked flask is placed 36.2 g. (0.55 mole) of zinc dust, and in a 250 ml. addition funnel is charged a solution of 80 ml. anhydrous benzene, 20 ml. of anhydrous ether, 80 g. (0.58 mole) of ρ-anisaldehyde and 98 g. (0.55 mole) of ethyl-2-bromopropionate. About 10 ml. of the solution is added to the zinc dust with vigorous stirring, and the mixture is warmed gently until an exothermic reaction commences. The remaining reactants are added dropwise at such a rate that the reaction mixture is refluxing smoothly on its own accord (ca. 30–35 min.) After addition is completed, the mixture is placed in a water bath and refluxed for 30 minutes. After cooling to 0°, 250 ml. of 10% sulfuric acid is added with vigorous stirring. The benzene layer is extracted twice with 50 ml. portions of 5% sulfuric acid, and washed twice with 50 ml. portions of 5% sulfuric acid and washed twice with 50 ml. portions of water. The aqueous acidic layers are combined and extracted with 2×50 ml. ether. The combined ethereal and benzene extracts are dried over sodium sulfate. Evaporation of solvent and fractionation of the residue through a 6" Vigreux column affords the product, ethyl-2-hydroxy-(ρ-methoxyphenyl)-1-methylpropionate, B.P. 155°–160° (1.5 mm).

By the method described in Vanden Zanden, Rec. trav. chim., 68, 413 (1949), the above compound is converted to 6-methoxy-2-methylindanone.

5-Ethyl-2-Methylindanone

The above reactions of Example 2A are repeated except that the starting materials are o-ethylbenzaldehyde and ethyl-2-bromopropionate. Using the same reaction conditions and techniques, there is obtained 5-ethyl-2-methylindanone.

When the benzaldehydes listed in Table I below are utilized in the procedure of Example 2A, the corresponding indanone is obtained.

TABLE I

| Aldehyde | Indanone |
|---|---|
| ρ-o-, or m-tolualdehyde | 2, 6-dimethyl, 2, 5-dimethyl, or 2, 4-dimethylindanone |
| ρ-o-, or m-hydroxybenzaldehyde | 4, 5 or 6-hydroxy-2-methylindanone |
| ρ-o-, or nitrobenzaldhyde | 2-methyl-(4, 5 or 6) nitroindanone |
| ρ-o-, or m-chlorobenzaldehyde | (4, 5, or 6) chloro-2-methylindanone |
| ρ-o-, or m-cyanobenzaldehyde | (4, 5, or 6) cyano-2-methylindanone |
| Vanillin | 6-hydroxy-5-methoxy 2-methylindanone |
| ρ-o-, or m-sulfamylbenzaldehyde | 2-methyl-(4, 5 or 6-sulfamylindanone |
| 3-chloro-4-methylbenzaldehyde | 5-chloro-2,6 dimethylindanone |
| 4-carbamide-5-methylbenaldehyde | 6-carbomide-2,5 dimethylindanone |
| 3,4-difluorobenzaldhyde | 5, 6 difluoro-2-methylindanone |

(B) 5-methoxy-2-methyl-1-(ρ-methylsulfonylbenzylidene)-3-indenyl acetic acid

The reactions of Examples 1C, 1D and 1E are repeated, and 5-methoxy-2-methyl-1-(ρ-methylsulfonylbenzylidene)-3-indenyl acetic acid is obtained. ($R_1$=hydrogen; $R_2$=$CH_3$; $R_3$=5—O—$CH_3$; $R_4$=hydrogen; $R_5$=p—$CH_3SO_2$)

Example 3

1-(ρ-Methylsulfonylbenzylidene-2-Methyl-5-Methoxy-3-Indenyl]-Propionic Acid (A) Methyl-α (5-methoxy-2-methyl-3-indenyl) propionate.

The procedure of Example 1C is followed using methyl α-bromopropionate in equivalent quantities in place of methyl bromoacetate used therein. There is obtained methyl α-(1-hydroxy-6-methoxy-2-methyl-1-indenyl)propionate, and it is then dehydrated to methyl α-(5-methoxy-2-methyl-3-indenyl)propionate in the same manner.

(B) α-[1-(ρ-methylthiobenzylidene)-2-methyl-5-methoxy-3-indenyl] propionic acid

To a solution of 0.5 g. (0.00192 mole) of methyl α-(5-methoxy-2-methyl-3-indenyl) propionate and 0.595 (0.0039 mole) of ρ-methylthiobenzaldehyde in 3 ml. of anhydrous pyridine is added 1.63 g. of a 40% solution of benzyltrimethylammonium hydroxide (Triton-B) in methanol. The resulting red-purple solution is stirred at room temperature overnight.

The reaction mixture is poured into a mixture of ice and water, acidified with 2.5N HCl, and extracted with ether. The ether solution is then washed with 2.5N HCl until the washing acidifies (once), then with water until neutral. The ether layer is then extracted with 5% $Na_2CO_3$ solution. The $Na_2CO_3$ solution is washed with ether, acidified and extracted with ether. The ether solution is washed with water, dried over $Na_2SO_4$ and concentrated in vacuo to a yellow oil that foams up to a clear yellow solid on pumping at 0.5–1 mm. Thin layer chromatography of the product shows only one spot when eluted with a (v./v. 4:3:5) of isopropanol: 10% $NH_4OH$: ethyl acetate mixture;

U.V. absorption: >max, 3525, 2910, 2540, 2450. E %, 399, 260, 510 and 498.

(C) α-[1-(p-methylsulfonylbenzylidene)-2-methyl 5-methoxy-3-indenyl]-propionic acid The procedure of Example 1E is followed using α-[1-(p-methylthiobenzylidene)-2-methyl-5-methoxy-3-indenyl]-propionic acid in place of 5-methoxy-2-methyl-1-(p-methylthiobenzylidene)-3-indenyl acetic acid thereby producing α-[1-(p-methylsulfinylbenzylidene)-2-methyl-5-methoxy-3-indenyl]-propionic acid (M.P. 115°–120°).

α-[1-(p-methylsulfonylbenzylidene-2-methyl-5-methoxy-3-indenyl]-propionic acid is produced following the procedure of Example 1E using the corresponding sulfoxide derivative.

($R_1$=CH$_3$; $R_2$ =CH$_3$; $R_3$=5-methoxy; $R_4$=hydrogen; $R_5$=CH$_3$SO$_2$—)

Example 4

1-p-Methylsulfonylbenzylidene-5-Dimethylamino-3-Indenyl Acetic Acid (A) Methyl-3-hydroxy-2-methyl-5-nitro-3-indenylacetate The procedure of Example 1C is followed using 2-methyl-6-nitro indanone in equivalent quantities in place of 6-methoxy-2-methyl-indanone used therein. After the mixture is condensed, 30 ml. of ethanol and 50 ml. of acetic acid are added. The mixture is then poured into 700 ml. of water. Extraction with ether gives methyl 3-hydroxy-2-methyl-5-nitro-3-indenylacetate.

(B) Methyl 5-dimethylamino-2-methyl-3-indenylacetate.

A solution of 0.05 mole of methyl 3-hydroxy-2-methyl-5-nitro-3-indenylacetate, 0.2 mole of 38% aqueous formaldehyde and 2 ml. of acetic acid in 100 ml. ethanol is reduced catalytically in the presence of a 10% Pd/C catalyst under 40 lb. p.s.i. hydrogen pressure at room temperature. The solution is filtered, evaporated and chromatographed on 300 g. of silica gel to give methyl 5-dimethylamino-3-hydroxy-2-methyl-3-indenylacetate. The hydroxy ester is then dehydrated to methyl 5-dimethylamino-2-methyl-3-indenylacetate.

(C) 1-p-methylthiobenzylidene-5-dimethylamino-2-methyl-3-indenyl acetic acid.

To a solution of 2.5 g. of the ester from Part B of this example in 15 ml. of 1,2-dimethoxyethane at 0° is added 1.5 g. of p-methylthiobenzaldehyde followed by 1.1 g. of potassium t-butoxlde. The reaction mixture is kept in the ice-bath for 4 hours, and then allowed to stand at room temperature for 18 hours. The mixture is diluted with 15 ml. of ether and the potassium salt is filtered. The salt is dissolved in 30 ml. of water and neutralized with dilute hydrochloric acid to pH 6–6.5. The crude acid precipitated is collected by filtration and chromatographed on a silica gel column, using ether-petroleum ether (v./v. 50–100%) as eluent to give pure 1-p-methylthiobenzylidene-5-dimethylamino-2-methyl-3-indenyl acetic acid which may be oxidized to 1-p-methylsulfinylbenzylidene-5-dimethylamino-2-methyl-3-indenyl acetic acid and 1-p-methylsulfonylbenzylidene-5-dimethylamino-2-methyl-3-indenyl acetic acid as described above.

($R_1$=hydrogen; $R_2$=CH$_3$; $R_3$=5—N(CH$_3$)$_2$; $R_4$=hydrogen; $R_5$=CH$_3$SO$_2$—)

Example 5

(1-p-Methylsulfonylbenzylidene)-2-Methyl-5-Dimethylamino-3-Indenyl-Propionic Acid (A) α-[1-(p-methylsulfonylbenzylidene)-2-methyl-5-dimethylamino-3-indenyl]-propionic acid.

The procedure of Examples 2A, B and C is followed using 6-dimethylamtno-2-methylindanone in place of 6-methoxy-2-methylindanone and methyl-α-bromopropionate in place of methyl bromoacetate used therein. There is obtained α-[1-(p-methylsulfonylbenzylidene)-2-methyl-5-dimethylamino-3-indenyl]-propionic acid.

($R_1$=CH$_3$; $R_2$=CH$_3$; $R_3$=5-dimethylamino; $R_4$=hydrogen; $R_5$=—CH$_3$SO$_2$)

Example 6

5,6-Difluoro-2-Methyl-1-(p-Methylsulfonylbenzylidene)-3-Indenyl Acetic Acid (A) 3,4-difluorobenzaldehyde.

In a 250 ml. three-necked flask equipped with a magnetic stirrer, thermometer, condenser, and dropping funnel is placed 25.6 g (0.2 mole) of 3,4 difluorotoluene. The liquid is heated to 105° and illuminated as 67 g. (0.42 mole) of bromine is added slowly. The temperature is kept between 105°–110° while the first half of the bromine is added over a period of one hour. The rest of the bromine is added over approximately a 2 hour period and the temperature is raised to 150° and kept there for 5 minutes. The reaction mixture is cooled and transferred to a 1 liter 3-necked flask with a motor driven stirrer and condenser. 120 ml. H$_2$O and 90 g. of calcium carbonate are added, and the mixture is refluxed for 20 hours with good stirring. The reaction mixture is steam distilled until no further oil is collected. The oil is taken up in methylene chloride and dried over MgSO$_4$. Evaporation of the solvent yields 3,4-difluorobenzaldehyde which is used without further purification.

(B) 3,4-difluoro-α-methylcinnamic acid.

A mixture of 2.88 g. (0.02 mole) of 3,4-difluorobenzaldehyde, 3.24 g. (0.025 mole) of propionic anhydride and 0.92 g. (0.02 mole) of sodium propionate under nitrogen is heated at 135° with a magnetic stirrer for 20 hours. The reaction mixture is poured onto 50 ml. of water. A solid precipitates that dissolves when 50 ml. of saturated K$_2$CO$_3$ is added with stirring. The basic solution is extracted with ether (2×100 ml.). The aqueous phase is then poured into an excess of concentrated HCl and ice. The precipitated white solid is filtered and dried to give 3,4-difluoro-α-methylcinnamic acid, M.P. 122°–125°.

4-Trifluoromethyl-α-Methylcinnamic Acid

The above reaction of Example 6A is repeated except that 4-trifluoromethylbenzaldehyde is used as a starting material in place of 3,4-difluorobenzaldehyde. Using the same reaction conditions and techniques there is obtained 4-trifluoromethyl-α-methylcinnamic acid.

Similarly using other benzaldehydes such as 4-methylthiobenzaldehyde, 4-chlorobenzaldehyde, and 3-methyl-4-chlorobenzaldehyde, there is obtained 4-methylthio-α-methylcinnamic acid, 4-chloro-α-methylcinnamic acid and 3-methyl-4-chloro-α-methylcinnamic acid respectively.

(C) 3,4-difluoro-α-methylhydrocinnamic acid.

28 g. (0.141 mole) of 3,4-difluoro-α-methylcinnamic acid, 1 g. of PtO$_2$ in 250 ml. of MeOH is hydrogenated at 45 p.s.i. until the theoretical uptake is completed. The catalyst is filtered off, and the material evaporated to one-third its volume. A 15% potassium hydroxide solution (10 ml.) is added, and the mixture refluxed for 30 minutes when it is poured into water and extracted with ether (2×100 ml.). The aqueous layer is acidified with concentrated HCl and ice. The oil which comes out is extracted into ether, the ether solution dried over MgSO$_4$ and evaporated to leave a Mwear oil which crystallizes. 3,4-difluoro-α-methylhydrocinnamic acid, M.P. 55°–56°, is isolated.

(D) 5,6-difluoro-2-methyl-1-indanone.

20 g. (0.1 mole) of 3,4-difluoro-α-methylhydrocinnamic acid is added to 250 g. of polyphosphoric acid. The mixture is efficiently stirred and heated on a steam bath for 2 hours. The mixture is poured onto ice-water (400 ml.). The precipitate is extracted with ether (3×100 ml.). The extract is washed with saturated potassium carbonate, water and then dried (MgSO$_4$). The ether solution, when evaporated, leaves solid 5,6-difluoro-2-methyl-1-indanone (M.P. 66°–68°) which is used without further purification.

(E) 5,6-difluoro-2-methylindene-3-acetic acid methyl ester.

A mixture of 9.1 g. (0.05 mole) of 5,6-difluoro-2-methyl-1-indanone, 4.0 g. of "activated" zinc dust, 7.6 g. (0.05 mole) of methyl bromoacetate, and a crystal of iodine in 250 ml. of dry benzene is refluxed for 4–5 hours. Tlc (20% Et$_2$O-80% pet. ether on Si gel) shows greater than 95% conversion at this time. The reaction mixture is poured onto 250 ml. of 5% H$_2$SO$_4$, separated, and dried (MgSO$_4$). Removal of solvent leaves an oily hydroxy ester. The crude ester is redissolved in 100 ml. of benzene and phosphorus pentoxide (20 g.) is added. The mixture is refluxed for 30 minutes (no stirrer necessary) and decanted. The residue is washed with benzene, the organic layers combined, washed with water (2×100 ml.) and dried (MgSO$_4$). The benzene, when evaporated, leaves 5,6-difluoro-2-methylindene-3-acetic acid methyl ester, M.P. 86°–90°.

5-Methylthio-2-Methylindene-3-Acetic Acid Methyl Ester

The above reaction of Example 6E is repeated using 5-methylthio-2-methylindanone instead of 5,6-difluoro-2-methyl-1-indanone. Using the same conditions and techniques, there is obtained 5-methylthio-2-methylindene-3-acetic acid methyl ester.

When an acylamino or sulfonyl indanone is employed as the starting material in the above procedure, the corresponding methyl ester is obtained.

(F) 5,6-difluoro-2-methyl-1-(p-methylthiobenzylidene)-indene-3-acetic acid.

1.19 g. (5.0 mole) of 5,6-Difluoro-2-methylindene-3-acetic acid methyl ester is dissolved in 10 ml. of dry pyridine followed by 0.76 g. (5.0 mole) of p-methylthiobenzaldehyde. The flask is placed under nitrogen, and 5.0 g (5.1 mole) of Triton B is added. The deeply colored solution is allowed to stand overnight, and then water (2 ml.) is added. After standing for 15 minutes, it is poured into an excess of water. The organics are extracted with ether (2×50 ml.). The aqueous phase is added to 10% HCl-ice. The orange, gummy solid that precipitates is extracted into methylene chloride and dried (MgSO$_4$). The solvent is removed to leave an orange solid. The solid is filtered to give a crude product which is recrystallized from benzene to give 5,6-difluoro-2-methyl-1-(p-methylthiobenzylidene)-indene-3-acetic acid. M.P. 181°–182.5°. When 3-methylthio-2-furaldehyde or 2-methylthio-5-pyrazine aldehyde is utilized in the above procedure instead of p-methylthiobenzaldehyde the corresponding indene acetic acid is obtained.

(G) 5,6-difluoro-2-methyl-1-(p-methylsulfonylbenzylidene)-indene-3-acetic acid.

To a solution of 0.358 g. (1.0 mole) of 5,6-difluoro-2-methyl-1-(p-methylthiobenzylidene)-indene-3-acetic acid in acetone (10 ml.) is added 10–15 ml. MeOH. With magnetic stirring, 0.32 g. (1.5 mole) of sodium meta periodate is added in 5 ml. of water. The proportions of acetone, methanol and water are adjusted if necessary to preserve homogeneity. After several minutes, a precipitation of sodium iodate appears. The suspension is stirred at room temperature for 16 hours, and then poured into approximately 50 ml. of water and 100 ml. methylene chloride. The two phases are separated and the water layer is extracted twice with methylene chloride. The organic phases are washed with water and dried (MgSO$_4$). The residue after evaporation is dissolved in the minimum amount of boiling ethyl acetate and allowed to stand for 12 hours in the freezer compartment. The deep orange crystals are filtered. The filtrate is reduced to ½ volume and allowed to stand in the cold for several hours to give a large second crop. In this way, 5,6-difluoro-2-methyl-1-(p-methylsulfinylbenzylidene)-3-indenylacetic acid is isolated, M.P. 200°–210°, which is converted to 5,6-difluoro-2-methyl-1-(p-methylsulfonylbensylidene)-3-indenylacetic acid with the procedure of Example 1. (R$_1$=hydrogen; R$_2$=CH$_3$; R$_3$=5-fluoro; R$_4$=6-fluoro; R$_5$=CH$_3$—SO$_2$).

Example 7

5,6-Difluoro-2-Methyl-1-(ρ-Methylsulfonylbenzylidene)-Indenyl-3-Acetic Acid (A) 5-6,difluoro-2-methyl-1-(ρ-methylsulfonylbenzylidene)-indene-3-acetic acid.

To 5,6-difluoro-2-methyl-1-(ρ-methylsulfinylbenzylidene)-indene-3-acetic acid (0.005 mole) in acetone (15 ml.) is added, slowly with stirring, m-chloroperbenzoic acid (0.005 mole). The mixture is heated and evaporated to near dryness at 40°. The solid is washed with boiling water (4×50 ml.) and dried yielding 5,6-difluoro-2-methyl-1-(ρ-methylsulfonylbenzylidene)-indene-3-acetic acid, M.P. 228°–230°. (R$_1$=hydrogen; R$_2$=CH$_3$; R$_3$=5-fluoro; R$_4$=6-fluoro; R$_5$=CH$_3$—SO$_2$—).

Example 8

5,6-Difluoro-2-Methyl-1-(ρ-Methylsulfonylbenzylidene)-3-Indenyl Acetic Acid (A) 3,4-difluorobenzaldehyde.

57 g. (0.5 mole) of ortho-difluorobenzene in 250 ml. of methylene chloride is added to 100 g. (0.75 mole) of anhydrous aluminum chloride. The mixture is stirred (motor) and cooled in an ice bath while 85.5 g. (0.75 mole) of dichloromethyl methylether is added dropwise. Vigorous HCl evolution takes place, and the reaction mixture turns orange-red. After the addition, the mixture is stirred at room temperature for 15 minutes, and the liquid phase is decanted into 500 ml. of ice and water. The unreacted residue of aluminum chloride is washed with methylene chloride until colorless, and the washings are added to the water. The mixture is shaken well in a separation funnel until the methylene chloride layer is green. The organic layer is washed with saturated potassium carbonate solution until neutral, then dried (MgSO$_4$) and distilled to give 3,4-difluorobenzaldehyde, B.P. 70°–74°/20 min. The dark residue in the distillation pot solidifies on cooling to give tris-(3-4,difluorophenyl)methane, M.P. 95°–96°.

3,4-Dimethylbenzaldehyde

The above reaction of Example 6A is repeated except that o-xylene and dichloromethyl methylether are the starting materials. Using the same reaction conditions and techniques, there is obtained 3,4-dimethylbenzaldehyde.

4-Mercaptobenzaldehyde

The above reaction of Example 6A is repeated except that the starting materials are mercaptobenzene and dichloromethyl methylether. Using the same reaction conditions and techniques, there is obtained 4-mercaptobenzaldehyde.

(B) 5,6-difluoro-2-methyl-1-(p-methylsulfonylbenzylidene)-3-indenyl acetic acid.

The reactions of Examples 6B, 6C, 6D, 6E, 6F and 6G are repeated and 5,6-difluoro-2-methyl-1-(p-methylsulfonylbenzylidene)-3-indenyl acetic acid is obtained. ($R_1$=hydrogen; $R_2$=$CH_3$; $R_3$=5-fluoro; $R_4$=6-fluoro; $R_5$=$CH_3SO_2$).

Similarly, when 3,4-dimethylbenzaldehyde is used in the reactions in Example 8B, 5,6-dimethyl-2-methyl-1-(p-methylsulfonylbenzylidene)-3-indenyl acetic acid is obtained.

When 6-mercaptobenzaldehyde is used in the reactions in Example 8B, 6-mercapto-2-methyl-1-(p-methylsulfonylbenzylidene)-3-indenyl acetic acid is obtained.

Example 9

α-(1-p-Methylsulfonylbenzylidene)-2-Methyl-5-Methoxy-6-Fluoro-3-Indenyl-Acetic Acid (A) 3-fluoro-4-methoxybenzaldehyde.

To a solution of o-fluoroanisole, 101 g. (0.80 mole) in 500 ml. dry methylene chloride is added dropwise over 30 minutes a solution of titanium tetrachloride, 182 g. (0.96 mole, 1.2 equiv.) and α,α-dichloromethylmethyl ether, 110 g. (0.96 mole) in an equal volume of methylene chloride. The temperature is maintained at 10°–20° C. with an ice-bath. The mixture is stirred at room temperature for 1 hour longer and then poured over crushed ice-water with stirring. Ether (1 l.) is added, and the mixture stirred under nitrogen until solution occurs. The organic layer is extracted with water (3×), sodium bicarbonate solution (3×) and dried ($MgSO_4$). The solvent is evaporated off at 30° to give crude product as an oil. The oil is vacuum distilled through a jacketed Vigreux column when it gives 3-fluoro-4-methoxybenzaldehyde, B.P. 120°–121° C., at 10 mm. Hg; $R_f$ 0.6 on a silica-gel G plate with methylene chloride.

(B) 3-fluoro-4-methoxy-α-methylcinnamic acid.

A mixture of 3-fluoro-4-methoxybenzaldehyde, 34.2 g. (0.22 mole), propionic anhydride, 50 g. (0.38 mole) and sodium propionate, 21 g. (0.22 mole) is stirred under nitrogen at 150° C. for 15 hours. The reaction mixture is then poured into 1.3 l. of water with stirring, and the product is precipitated. 2.0N potassium hydroxide solution (500 ml.) is added, and the mixture stirred for several hours, until the acid has dissolved.

The aqueous solution is extracted with ether (3×) and then acidified with concentrated hydrochloric acid with stirring. The precipitated product is collected, washed thoroughly with water and dried in a vacuum oven at 50° C. over potassium hydroxide pellets to give 3-fluoro-α-methyl-4-methoxycinnamic acid, M.P. 167°–169° C.; $R_f$ 0.5 on silica-gel G with methylene chloride-methanol (1:1).

(C) 3-fluoro-4-methoxy-α-methyl dihydrocinnamic acid.

3-Fluoro-4-methoxy-α-methylcinnamic acid, (49.5 g.; 0.236 mole) in 800 ml. methanol is hydrogenated at 43 lbs. pressure and room temperature until the theoretical uptake of hydrogen has occurred (24 min at 20° C., using 1.5 g. platinum oxide catalyst). The solution is filtered and then evaporated with warming to 60° to give 3-fluoro-4-methoxy-α-methyl dihydrocinnamic acid, $R_f$ 0.5 on silica-gel G with methylene chloride-methanol (9:1).

(D) 5-fluoro-6-methoxy-2-methylindanone.

A mixture of 3-fluoro-α-methyl-4-methoxy dihydrocinnamic acid, 49.3 g. (0.23 mole) in 500 g. of polyphosphoric acid is heated at 95° C. on a steam bath with occasional agitation for 75 min. The dark red solution is poured into 3.0 liters of water, and the mixture is stirred overnight. The precipitated product is collected, washed thoroughly with water and then taken up in ether. The ether solution is extracted with aqueous potassium bicarbonate (4×), diluted with methylene chloride, and dried ($MgSO_4$).

The organic solution is evaporated and recrystallized from methylene chloride-petroleum ether to give 5-fluoro-6-methoxy-2-methylindanone, (M.P. 76°–78°).

(E) Methyl 6-fluoro-5-methoxy-2-methyl-3-indenylacetate.

Into a 500 ml. three-necked flask fitted with mechanical stirrer, reflux condenser, drying tube, dropping funnel and nitrogen inlet is placed 8.0 g. zinc sheet and 100 ml. of dry benzene. A few milliliters of a solution of 21.3 g. (0.11 mole) of 5-fluoro-6-methoxy-2-methylindanone and 18.36 g. (0.121 mole) of methyl bromoacetate in 100 ml. of dry benzene is added at a time. A crystal of iodine is added. The mixture is gently heated with stirring. After the iodine color has disappeared, the remainder of the mixture is added gradually. The reaction is heated at reflux temperature for about 18 hours. The mixture is poured onto 600 ml. of 5% $H_2SO_4$ and about 500 g. of ice. Some ether is added. The organic layer is separated and washed with three portions of 5% $H_2SO_4$ water, $KHCO_3$ solution and finally water again. The organic layer is dried ($MgSO_4$) and concentrated to give 27.6 g. of reddish oil which crystallizes upon standing. Thin-layer chromatography on silica-gel G with methylene chloride methanol (99:1) shows product at $R_f$ (0.5).

Without further purification, the hydroxy ester is dehydrated to the indenylacetate. In 200 ml. of dry benzene, 14.2 g. (53 mole) of crude ester and 36 g. of phosphorus pentoxide are refluxed with stirring for ½ hour. After cooling, the reaction mixture is filtered and the solid residue washed well with benzene. The benzene filtrate is washed with two portions of salt water and dried ($MgSO_4$). The organic solution is concentrated and gives a slightly colored oil which rapidly crystallizes. The crude product is recrystallized from methylene chloride-petroleum ether to give methyl-6-fluoro-5-methoxy-2-methyl-3-indenylacetate (M.P. 61°–62°).

(F) 6-fluoro-5-methoxy-2-methyl-1-(p-methylthiobenzylidene)-3-indenyl acetic acid.

To a solution of methyl-6-fluoro-5-methoxy-2-methyl-3-indenyl acetate, 9.3 g. (0.037 mole) and p-methylthiobenzaldehyde, 6.3 g. (1.1 equivalent) is added 16 ml. (2.0 equivalents) of 25% methanolic sodium methoxide. The mixture is stirred at reflux under nitrogen for 2 hours. An equal volume of water is added dropwise and refluxing continues for 30 minutes. The solution is cooled, diluted with water and extracted with ether (3×). Residual ether is blown off with nitrogen, and then the aqueous solution is acidified with 50% glacial acetic acid. The precipitated product is collected and washed thoroughly with water. The crude product is recrystallized from methanol to give 6-fluoro-5-methoxy-2-methyl-1-(p-methylthiobenzylidene)-2-indenyl acetic acid, M.P. 172°–174°.

(G) 6-fluoro-5-methoxy-2-methyl-1-(p-methylsulfonylbenzylidene)-3-indenyl acetic acid.

A solution of sodium periodate, 4.28 g. (20 mole) in 40 ml. of water is added dropwise to 6-fluoro-5-methoxy-2-methyl-1-(p-methylthiobenzylidene)-3-indenyl acetic acid, 3.70 g. (10 mole) in 300 ml. methanol and enough acetone to cause solution. This solution is stirred over night at room temperature and filtered. The filtrate is evaporated at 30° to a small volume which causes the product to precipitate. The suspension is diluted with several volumes of water, cooled and collected. After rinsing with water and cold methanol-water (1:1), the product is dried in vacuo over potassium hydroxide pellets, and then in a vacuum oven at 70° C. The crude product is recrystallized from methylene chloride-petroleum ether to give 6-fluoro-5-methoxy-2-methyl-1-(p-methylsulfinylbenzylidene)-3-indenyl acetic acid (M.P. 190°–193°).

6-Fluoro-5-methoxy-2-methyl-1-(p-methylsulfonylbenzylidene)-3-indenyl acetic acid is prepared according to the procedure of Example 7 by the addition of 1.0 mole of m-chloroperbenzoic acid per mole of 6-fluoro-5-methoxy-2-methyl-1-(p-methylsulfinylbenzylidene)-3-indenyl acetic acid in an acetone solution.

α-[1-(p-Methylsulfonylbenzylidene)-2-methyl-5-methoxy-6-fluoro-3-indenyl]-propionic acid is prepared by the procedures of Examples 3A, 3B and 3C. ($R_1$=hydrogen; $R_2$=$CH_3$; $R_3$=5—$CH_3$—O—; $R_4$=hydrogen; $R_5$=$CH_3$—$SO_2$—)

Example 10

α-(1-p-Methylsulfonylbenzylidene)-2-Methyl-5-Fluoro-3-Indenyl-Acetic Acid (A) p-Fluoro-α-methylcinnamic acid.

p-Fluorobenzaldehyde (200 g., 1.61 mole), propionic anhydride (3.5 g., 2.42 mole) and sodium propionate (155 g., 1.61 mole) are mixed in a 1 l. three-necked flask which had been flushed with nitrogen. The flask is heated gradually in an oil-bath to 140°. After 20 hours, the flask is cooled to 100° and poured into 8 l. of water. The precipitate is dissolved by adding potassium hydroxide (302 g.) in 2.1 of water. The aqueous solution is extracted with ether, and the ether extracts washed with potassium hydroxide solution. The combined aqueous layers are filtered, acidified with concentrated HCl, filtered and the collected solid washed with water, thereby producing p-fluoro-α-methylcinnamic acid which is used as obtained.

(B) p-Fluoro-α-methylhydrocinnamic acid.

To p-fluoro-α-methylcinnamic acid (177.9 g., 0.987 mole) in 3.6 l. ethanol is added 11.0 g. of 5% Pd/C and the mixture is reduced at room temperature under a hydrogen pressure of 40 p.s.i. Uptake is 31/32 lbs. (97% of theoretical). After filtering the catalyst, the filtrate is concentrated in vacuo to give the product p-fluoro-α-methylhydrocinnamic acid used without weighing in next step.

(C) 6-Fluoro-2-methylindanone.

To 932 g. polyphosphoric acid at 70° on the steam bath is added p-fluoro-a-methylhydrocinnamic acid (93.2 g., 0.5 mole) slowly with stirring. The temperature is gradually raised to 95° C., and the mixture kept at this temperature for 1 hour. The mixture is allowed to cool and added to 2 l. of water. The aqueous layer is extracted with ether, the ether solution washed twice with saturated sodium chloride solution, 5% $Na_2CO_3$ solution, water, and then dried. The ether filtrate is concentrated with 200 g. silica-gel, and added to a five pound silica-gel column packed with 5% ether-petroleum ether. The column is eluted with 5–10% ether-petroleum ether and followed by TLC to give 6-fluoro-2-methylindanone.

(D) 5-fluoro-2-methylindanone-3-acetic acid.

A mixture of 6-fluoro-2-methylindanone (18.4 g., 0.112 g. mole), cyanoacetic acid (10.5 g., 0.123 mole), acetic acid (6.6 g.), and ammonium acetate (1.7 g.) in dry toluene (15.5 ml.) is refluxed with stirring for 21 hours, as the liberated water is collected in a Dean Stark trap. The toluene is concentrated, and the residue dissolved in 60 ml. of hot ethanol and 14 ml. of 2.2N. aqueous potassium hydroxide solution. 22 g. of 8.5% KOH in 150 ml. of water is added, and the mixture refluxed for 13 hours under nitrogen. The ethanol is removed under vacuum, 500 ml. water added, the aqueous solution washed well with ether and then boiled with charcoal. The aqueous filtrate is acidified to pH 2 with 50% hydrochloric acid, cooled and the precipitate collected. In this way dried 5-fluoro-2-methylindenyl-3-acetic acid (M.P. 164°–166°) is obtained (E) 5-fluoro-2-methyl-1-(p-methylthiobenzylidene)-3-indenyl acetic acid.

5-fluoro-2-methyl-3-indenyl acetic acid (15 g., 0.072 mole) p-methylthiobenzaldehyde (14.0 g., 0.091 mole) and sodium methoxide (13.0 g., 0.24 mole) are heated in methanol (200 ml.) at 60° under nitrogen with stirring for 6 hours. After cooling, the reaction mixture is poured into 750 ml. of ice-water, acidified with 2.5N hydrochloric acid, and the collected solid triturated with a little ether to produce 5-fluoro-2-methyl-1-(p-methylthiobenzylidene)-3-indenyl acetic acid (M.P. 187°–188.2°). U.V. in methanol $\lambda_{max}$. 348 mμ (E % 500), 258 (557), 258 (495), 353 (513), 262.5 (577), 242.5. (511).

(F) 5-fluoro-2-methyl-1-(p-methylsulfinylbenzylidene)-3-indenyl acetic acid.

To a solution of 5-fluoro-2-methyl-1-(p-methylthiobenzylidene)-3-indenyl acetic acid (3.4 g., 0.01 mole) in a mixture of methanol (250 ml.) and acetone (100 ml.) is added a solution of sodium periodate (3.8 g., 0.018 mole) in water (50 ml.) with stirring.

Water (450 ml.) is added after 18 hours, and the organic solvents removed under vacuum below 30°. The precipitated product is filtered, dried and recrystallized from ethyl acetate to give 5-fluoro-2-methyl-1-(p-methylsulfinylbenzylidene)-3-indenyl acetic acid. Upon repeated recrystallization upon ethylacetate there is obtained cis-5-fluoro-2-methyl-1-(p-methylsulfinylbenzylidene)-3-indenyl acetic acid, M.P. 184°–186°. U.V. in methanol; $\lambda_{max}$ 328 (E % 377), 286 (432), 257.5 shldr. (413), 227 (548).

Further runs reveal the existence of a second polymorph of cis-5-fluoro-2-methyl-1-(p-methylsulfinylbenzylidene)-3-indenyl acetic acid, M.P. 179°–181° C.

5-chloro-2-methyl-1-(p-methylsulfinylbenzylidene)-3-indenyl acetic acid is prepared by the procedure as described previously in this Example 10, and can be converted to the corresponding sulfonyl compound by the procedure set forth below.

5-fluoro-2-methyl-1-(p-methylsulfonylbenzylidene)-3-indenyl acetic acid is prepared by adding sodium methoxide (4.4M in MeOH, 68.5 ml, 0.3 mol) dropwise to a stirred cooled mixture of 5-fluoro-2-methyl-1-(p-methylsulfinylbenzylidene)-3-indenyl acetic acid (100 g, 0.281 mol) in methanol (250 ml) and acetonitrile (500 ml).

Sodium bicarbonate (0.56 mol) and hydrogen peroxide (30% in water, 0.56 mol) are added and allowed to react for 18 hours at −10° C. Excess sodium bicarbonate is filtered off, and cooled filtrate (0° C.) neutralized dropwise to pH 7 with 1M hydrochloric acid (350 ml). The resulting product is then filtered and washed with methanol. A thin layer chromatography system to check for purity utilizes chloroform:methyl isobutyl ketone (8:2); the $R_f$ value is 0.21. A tetrahydrofuran/diisopropyl ether combination can be used for product recrystallization. Reaction yield is 89%. The product has a mp of 205°–206° C. ($R_1$=hydrogen; $R_2$=$CH_3$; $R_3$=5-fluoro; $R_4$=hydrogen; $R_5$=$CH_3SO_2$—)

α-[1-(p-Methylsulfonylbenzylidene)-2-methyl-5-fluoro-3-indenyl]-propionic acid is prepared by the procedures of Examples 3A, 3B and 3C.

Example 11

Cis-5,7-Difluoro-2-Methyl-1-(ρ-Methylsulfonylbenzylidene)-3-Indenyl Acetic Acid (A) 2,4-difluorobenzaldehyde.

A 250 ml., three-necked flask is fitted with a stirrer, a thermometer, a dropping funnel with a long stem to the bottom of the flask and a reflux condenser with a tube leading to the back of a hood. 50 g. (0.38 mole) of 2,4-difluorotoluene is heated to reflux with stirring and irradiated with a Hanovia ultraviolet lamp. 41.5 ml. of bromine is gradually added. The reaction is completed in 2.5 hours during which time the reflux temperature rises from 112° to 155°.

A 2 l. three-necked flask is fitted with a stirrer and reflux condenser. In the flask is placed 200 ml. of water and 140 g. calcium carbonate. The cooled above-described reaction mixture is transferred using some ether for rinsing. The hydrolysis is completed by refluxing with stirring for 18 hours. The aldehyde is isolated by steam distillation from the reaction flask. The oil is separated and the aqueous phase is extracted once with ether. The combined oil and ether extract is dried over anhydrous $MgSO_4$ and concentrated under reduced pressure to leave 2,4-difluorobenzaldehyde, still containing some ether which is distilled through a short Vigreux column under reduced pressure and separated into several fractions. These are combined to give 2,4-difluorobenzaldehyde, B.P. 56°–58° 12 mm.

(B) 2,4-difluoro-α-methylcinnamic acid.

A 500 ml., three-necked flask is fitted with reflux condenser, drying tube, stirrer and $N_2$ inlet. To a mixture of 55.4 g. (0.39 mole) of 2,4-difluorobenzaldehyde and 56 ml. of propionic anhydride is added 38 g. (0.39 mole) of sodium propionate. The reaction mixture is heated at 135°–140° (oil bath temp.) for 19 hours with stirring under nitrogen. The still warm solution is poured into 1 l. of water with stirring. A solid separates, which upon adding 56 g. of potassium hydroxide, dissolves. The solution is extracted with ether, and then heated on the steam bath to remove the ether. After cooling in an ice-bath, concentrated hydrochloric acid is added with stirring. The product which separates is collected and washed with cold water. After drying at 60° over KOH, 2,4-difluoro-α-methylcinnamic acid, M.P. 126°–128° is obtained.

(C) 2,4-difluoro-α-methylcinnamic acid.

In 800 ml. of methanol, 60 g. (0.3 mole) of 2,4-difluoro-α-methylcinnamic acid with 1.5 g. of platinum oxide catalyst is shaken under an initial pressure of 42 lbs. of hydrogen until one equivalent of hydrogen is absorbed. The reaction time is 30 minutes. The catalyst is removed by filtration and washed with methanol. The methanol, when evaporated off, leaves near colorless 2,4-difluoro-α-methyldihydrocinnamic acid as an oil which is used in the next step without further purification.

(D) 4,6-difluoro-2-methylindanone.

A solution of 2,4-difluoro-α-methyldihydrocinnamic acid, 54.8 g. (0.274 mole) in 125 ml. thionyl chloride is stirred for 90 minutes, and then at reflux for 90 minutes longer. The reaction solution is evaporated under reduced pressure leaving the acid chloride product as an oil.

To a suspension of ice-bath cooled anhydrous powdered aluminum chloride, 60 g. (0.45 mole), in 250 ml. of dry carbon disulfide is added dropwise over 10 minutes, a solution of the acid chloride, 60 g., in 100 ml. carbon disulfide. After the addition, the ice bath is removed, and the temperature raised slowly to room temperature. The mixture is stirred at room temperature for 20 hours, and then is poured into 2 l. of 10 aqueous hydrochloric acid—crushed ice with stirring. Ether is added, and the stirring continued until everything dissolves. The ether layer is extracted with 5% hydrochloric acid (2×), water (2×), and sodium bicarbonate solution (2×), when it is diluted with methylene chloride and dried ($MgSo_4$). The filtered solution is evaporated with warming to 70° C. to give the crude 4,6-difluoro-α-methylindanone as an oil which crystallizes on standing. The crude product is purified by chromatography of a column (7.0×35 cm.) of silica-gel, 400 g. of J. T. Baker 3405 packed in petroleum ether-methylene chloride (2:1). The column is developed and eluted with the same solvent system, and upon recrystallization from methylene chloride-petroleum ether gives 4,6-difluoro-2-methylindanone, M.P. 68°–69° C.

(E) Methyl 5,7-difluoro-2-methylindenyl-3-acetate.

About 20% of a solution containing 4,6-difluoro-2-methylindanone, 15.0 g. (83 mole), and methyl bromoacetate, 14.0 g. (1.1 equiv.) in 100 ml. dry benzene is added to a stirred suspension of powdered zinc dust (Merck dried 120°/22 mm.), 6.5 g. (1.2 equiv.) in 74 ml. dry benzene under a nitrogen atmosphere. Several crystals of iodine are added, and the mixture slowly brought to a reflux. The remainder of the solution is added dropwise over 10 minutes, and the mixture stirred at reflux overnight, i.e., 17 hours. The reaction is cooled to room temperature, the mixture poured into 2.0 l. of 20% aqueous sulfuric acid-crushed ice with stirring, and ether added until a clear solution is obtained. The ether layer is extracted with 5% aqueous sulfuric acid (3×), water (3×), diluted with methylene chloride and dried ($MgSO_4$). The filtered ethereal solution is evaporated to give crude hydroxy ester.

Powdered phosphorus pentoxide (60.0 g.) is added to the hydroxy ester (20.0 g.) in 400 ml. of dry benzene. The mixture is stirred at reflux for 30 minutes, and the clear benzene solution decanted. The residue is rinsed with benzene and then with ether. The combined organic solutions are diluted with ether, extracted six times with aqueous sodium sulfate solution, twice with aqueous potassium bicarbonate solution, diluted with methylene chloride and dried ($MgSO_4$). The crude indenyl acetate product is obtained by evaporation of the filtered elution to give an oil. The product is crystallized from petroleum ether and gives methyl 5,7-difluoro-2-methylindenyl-3-acetate, M.P. 69°–70° C.

(F) 5,7 difluoro-2-methyl-1-(p-methylthiobenzylidene)-3-indenyl acetic acid, a mixture of geometric isomers.

Powdered sodium methoxide, 2.2 g. (40 mole) is added to a suspension of methyl 5,7-difluoro-2-methyl-indenyl-3- acetate (4.78 g.) (20 mole) and p-methylthiobenzaldehyde, 3.35 g. (22 mole), in 40 ml. dry methanol under nitrogen. A clear solution results which is refluxed for 60 minutes. An equal volume of water is added, and refluxing continued under nitrogen for 30 minutes to complete saponification. The solution is diluted with several volumes of water and extracted with ether. Nitrogen is bubbled through the aqueous solution to remove the residual ether solvent. Fifty percent aqueous acetic acid (40 ml.) is used to precipitate the product. The product is collected and washed well with water. Then it is dried in a desiccator over potassium hydroxide pellets, and finally in the oven at 100°. The crude product is recrystallized from methylene chloride-petroleum ether and gives a mixture of the cis and trans isomers of the acid, M.P. 164°–173° in a 1:3 ratio, identifiable by integrating the 2—$CH_3$ signal in the N.M.R. spectra at 7.82 γ for cis and 8.20 γ for trans.

(G) Cis-methyl-5,7-difluoro-2-methyl-1-(ρ-methylthiobenzylidene)-3-indenylacetate isolation by column chromatography.

Four drops of concentrated sulfuric acid are added to a solution of 5,7-difluoro-2-methyl-1-(ρ-methylthiobenzylidene)-3-indenyl acetic acid, 1.0 g. (2.8 mole) in 60 ml. of dry methanol, and the solution stirred at reflux overnight. The solution is cooled and crystals separated which are collected, rinsed with cold methanol-water (1:1) and dried over potassium hydroxide pellets. These crystals are found to be about 95% of the trans-isomer, and could be further purified by recrystallizing from methanol giving the trans-isomer, M.P. 106°–106.5° C. Powdered potassium bicarbonate is added to the filtrate from the first crop of crystals, followed by water. A second crop of mixed ester is obtained in this way which is cis-enriched and used for chromatography.

1.7 g. of cis and trans-mixed esters are chromatographed on a column (3.0×90 cm.) of silica-gel, 250 g. of J. T. Baker 3405, packed in methylene chloride-petroleum ether (1:9). The column is developed and eluted with a 1:4 ratio of the same solvents. 0.3 to 0.4 l. cuts are taken as the yellow bands are eluted. In this way the trans-isomer and the cis-isomer (M.P. 94°–94°) are obtained; U.V. of trans in MeOH $_{max}$ 217 mμ., 256 and 362 mμ; U.V. of cis-isomer in MeOH λmax$_{218}$ mμ., 260 and 357 mμ.

(H) Cis-5,7-difluoro-2-methyl-1-(ρ-methylthiobenzylidene)-3-indenyl acetic acid.

1.0N aqueous sodium hydroxide 3.0 ml. (3.0 mole) is added to cis-methyl 5,7-difluoro-2-methyl-1-(ρ-methylthiobenzylidene)-3-indenylacetate, 250 mg. (0.64 mole) in 20 ml. methanol under nitrogen. The mixture is refluxed for 1 hour, cooled, diluted with water and acidified with several ml. of 50% acetic acid. Crystals form and after further chilling in ice bath, they are collected, worked thoroughly with water and sucked nearly dry. The product is recrystallized from methanol-water, dried over potassium hydroxide pellets in a vacuum desiccator and finally in a vacuum oven at 100°. In this way cis-5,7-difluoro-2-methyl-1-(ρ-methylthiobenzylidene)-3-indenyl acetic acid (M.P. 182°–184°) is obtained.

(I) Cis-5,7-difluoro-2-methyl-1-(ρ-methylsulfonylbenzylidene)-3-indenyl acetic acid.

Sodium periodate 214 mg. (1.0 mole) in 2 ml. water is added to cis-5,7-difluoro-2-methyl-1-(ρ-methylthiobenzylidene)-3-indenyl acetic acid, 170 mg. (0.475 mole) in 12 ml. of methanol and about 0.5 ml. of acetone at room temperature. The mixture is stirred overnight when inspection of tlc on silica-gel G using methylene chloride-methanol elution (1:1) shows that there is no starting material present but a trace of sulfone at $R_f$ 0.55. The reaction mixture is filtered and concentrated to a small volume without heating and diluted with water. The product is collected, rinsed with water and dried over potassium hydroxide pellets in a vacuum desiccator and finally in the oven desiccator at 80°. The product is recrystallized from ethyl acetate-petroleum ether and gives pure cis-5,7-difluoro-2-methyl-1-(ρ-methylsulfinylbenzylidene)-3-indenyl acetic acid, M.P. 188°–189° C., which is converted to cis-5,7-difluoro-2-methyl-1-(ρ-methylsulfonylsulfonylbenzylidene)-3-indenyl acetic acid in the procedure of Example 1E. ($R_1$=hydrogen; $R_2$=$CH_3$; $R_3$=5-fluoro; $R_4$=7-fluoro; $R_5$=$CH_3SO_2$)

Example 12

α-(1-Methylsulfonylbenzylidene-2-Methyl-5,6-Difluoro-3-Indenyl)-Propionic Acid

α-[1-ρ-methylsulfinylbenzylidene)-2-methyl-5,6-difluoro-3-indenyl]-propionic acid (0.01 mol.) is prepared by the procedure of Example 3A, B and C, and converted to the sulfonyl derivative using the procedure of Example 1E. The procedure yields the desired compound ($R_1$=hydrogen; $R_2$=$CH_3$; $R_3$=5-fluoro; $R_4$=6-fluoro; $R_5$=$CH_3SO_2$).

Example 13

α-(1-ρ-Methylsulfonylbenzylidene-2-Methyl-5-Fluoro-6-Methoxy-3-Indenyl)-Propionic Acid α-[1-(ρ-methylsulfinylbenzylidene)-2-methyl-5-fluoro-6-methoxy-3-indenyl]-propionic acid is prepared by the procedures of Examples 3A–3C, and converted to the sulfonyl derivative using the procedure of Example 1E ($R_1$=methyl; $R_2$=methyl; $R_3$=5-fluoro; $R_4$=6-methoxy; $R_5$=$CH_3$—$SO_2$).

Example 14

α-(1-ρ-Methylsulfonylbenzylidene-2-Methyl-5-Fluoro-3-Indenyl)-Propionic Acid

α-[1-(ρ-methylsulfinylbenzylidene)-2-methyl-5-fluoro-3-indenyl propionic acid is prepared by the procedures of Examples 3A–3C, and converted to the sulfonyl derivative using the procedure of Example 1E ($R_1$=methyl; $R_2$=methyl; $R_3$=5-fluoro; $R_4$=hydrogen; $R_5$=$CH_3$—$SO_2$).

Example 15

N-[5-fluoro-2-methyl-1-(ρ-methylsulfonylbenzylidene)-3-indenylacetyl]glycine (A) Benzyl-N-[5-fluoro-2-methyl-1-(ρ-methylsulfinylbenzylidene)-3-indenylacetyl]-glycinate. The procedure of Example 14 is followed using benzylamine acetate in place of the morpholine to produce the above-named compound.

(B) N-[5-fluoro-2-methyl-1-(ρ-methylsulfinylbenzylidene)-3-indenylacetyl]-glycine. Benzyle-N-[5-fluoro-2-methyl-1-(ρ-methylsulfinylbenzylidene)-3-indenylacetyl]-glycinate (0.03 mole) in a mixture of 25 ml. of anhydrous ethanol and 2.5 ml. of 1N sodium hydroxide is allowed to stand at room temperature for 18 hours. The solution is diluted with water and extracted with ether. The aqueous layer is acidified with dilute hydrochloric acid and the organic product is extracted with ethyl acetate, washed with water and dried over sodium sulfate. Evaporation of the solution gives N-[5-fluoro-2-methyl-1-(ρ-methylsulfinylbenzylidene)-3-indenylacetic acid, the corresponding indenyl acyl glycine is obtained, which can be converted to the corresponding sulfonyl derivative using the procedure of Example 1E.

Example 16

(A) Sodium 5-fluoro-2-methyl-1-(ρ-methylsulfonyl-benzylidene)-3-indenylacetate 5-fluoro-2-methyl-1-(ρ-methylsulfonylbenzylidene)-3-indenylacetic acid (1.79 g.) in methanol (10 ml.) is added to a solution of sodium methoxide (0.27 g.) in methanol (5 ml.). The reaction mixture is stirred for 20 minutes and evaporated to dryness to yield sodium 5-fluoro-2-methyl-1-(ρ-methylsulfonylbenzylidene)-3-indenylacetate.

(B) Calcium 5-fluoro-2-methyl-1-(ρ-methylsulfonylbenzylidene)-3-indenylacetate

The above reaction is repeated using 2 moles of acid per mole of calcium methoxide. Using the same reaction conditions and techniques there is obtained calcium 5-fluoro-2-methyl-1-(ρ-methylsulfonylbenzylidene)-3-indenylacetate.

Example 17

5-Methoxy-2-methyl-1-(ρ-methyl-sulfonylbenzylidene)-3-indenyl-γ-trans-crotonic acid According to procedures C & D in Example 1, 6-methoxy-2-methylindanone is allowed to react with γ-bromocrotonic acid methyl ester to give the desired methylthio product.

Similarly, if any of the other indanones listed in Table I and synthesized according to Example 2 are used in the above procedure with either γ-bromocrotonic acid methyl ester or with γ-bromo-γ-methylcrotonic acid methyl ester, the corresponding indenylcrotonic acids are obtained. All of these are oxidized from methylthio to methyl sulfonyl compounds with periodate according to Example 1E.

Example 18

5-methoxy-2-methyl-1-(ρ-methylsulfonyl-cinnamilydene)-3-indenyl-acetic acid

According to procedure D in Example 1, methyl 5-methoxy-2-methyl-3-indenyl acetate is condensed with ρ-methylthio cimamaldehyde to give the desired methylthio product, which can be oxidized according to procedure 1E to the title compound.

Similarly, if other 3-indenyl acetates, propionates or crotonates (See Example 17) are used, the corresponding sulfonyl compounds are obtained, after oxidation of the intermediate methylthio compounds according to Example 1E.

Example 19

α-(1-ρ-Methylsulfonylbenzylidene)-2-Methyl-5-Fluoro-3-Indenyl-Acetic Acid Methyl Ester 5-fluoro-2-methyl-1-(ρ-methylsulfonylbenzylidene)-3-indenyl acetic acid is prepared by the procedure of Example 10, and converted to the methyl ester derivative by the following procedure. Sodium methoxide (4.4M in methanol, 1.36 ml, 0.006 mol) is added to a stirred cooled solution (0° C.) of 5-fluoro-2-methyl-1-(ρ-methylsulfonylbenzylidene)-3-indenyl acetic acid (1.04 g, 0.0028 mol) in methanol (5 ml) and acetonitrile (10 ml). After 30 min, the reaction mixture is dropped into concentrated hydrochloric acid (50 ml) and extracted with methylene chloride (3×25 ml). The organic layer is extracted with saturated sodium bicarbonate (3×25 ml), dried with sodium sulfate, and concentrated in vacuo. The resulting oil is crystallized from tetrahydrofuran/hexane to yield 0.2 g of the desired compound. The melting point is 165°–166° C. ($R_1$=hydrogen; $R_2$=$CH_3$; $R_3$=5-fluoro; $R_4$=hydrogen; $R_5$=$CH_3SO_2$—; M=$OCH_3$) Other methyl esters of compounds of this invention can be prepared in a similar fashion.

Example 20

Biological Effects

The compounds of Examples 10 and 19 were assayed for their effect on various cell lines to ascertain the degree of growth inhibition following treatment with compounds of this invention. Cytotoxicity data obtained using these cell lines is thought to be indicative of the effect on precancerous lesions. The cell lines employed for these experiments were well characterized, and are used by the United States National Cancer Institute in their screening program for new anti-cancer drugs.

Tumor cell cytotoxicity was assessed using the Sulforhodamine B Assay. In this assay, tumor cells were plated in 96-well plates and treated with drug-containing media for seven days (continuous exposure). At the end of the exposure period, the cells were fixed and stained with sulforhodamine B (a pink fluorescent dye). The dye was then solubilized, and the optical density of the resulting pink solution determined on a 96-well plate reader. The mean dye intensity of the treated wells was then divided by the mean dye intensity in the control wells (6 wells of each) to determine the effect of the drug on the cells. Dye intensity is proportional to the number of cells or amount of protein per well. The resultant "percent of control" value then represents the degree of growth inhibition caused by the drug.

For each experiment, an $IC_{50}$ value was determined and used for comparative purposes. This value is equivalent to the concentration of drug needed to inhibit tumor cell growth by 50%. $IC_{50}$ values were obtained graphically by connecting the mean values for each drug concentration tested. Each experiment included at least six wells per drug concentration. Concentration was plotted on a log scale on the X-axis. The $IC_{50}$ values obtained are provided in Table I below.

TABLE I

| Cell Line | Type | $IC_{50}$ Values (μM) Example 10 | Example 19 |
|---|---|---|---|
| SW480 | Colonic Adenocarcinoma of epithelial origin | 141 | — |
| Ht-29 | Colonic Adenocarcinoma - moderately well defined | 183 | >100 |
| DLD-1 | Colonic Adenocarcinoma | 51 | — |
| A-427 | Lung Carcinoma | 128 | — |
| MCF-7 | Breast Carcinoma | 90 | 63 |
| UACC 375 | Melanoma Line | 90 | 40 |

The compounds of Examples 1–19 can be formulated with pharmaceutically acceptable carriers into unit dosage forms in a conventional manner so that the patient in need of therapy for precancerous lesions can periodically (e.g. once or more per day) take a compound according to the method of this invention. It has been found that colonic bacteria will convert the sulfonyl derivatives in part to still unidentified metabolite(s). Specifically, when cis-5-fluoro-2-methyl-1-[p-(methylsulfonyl)benzylidene]indene-3-acetic acid prepared according to the procedure of Example 10 is introduced into an anerobic chamber containing an aqueous suspension of human fecal material, and incubated for 1 to 24 hours, the sulfonyl compound is converted to an unknown derivative, as verified by high pressure liquid chromatography.

The exact initial dose of the sulfonyl derivatives used in the method of this invention can be determined with reasonable experimentation, but is believed to be larger than that found to be effective for sulindac.

It will be understood that various changes and modifications can be made in the details of procedure, formulation and use without departing from the spirit of the invention, especially as defined in the following claims.

We claim:

1. A method for inhibiting growth of precancerous lesion cells, comprising exposing said cells, in the absence of sulindac, to a growth inhibiting effective amount of a compound of the formula B:

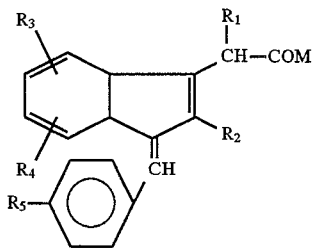

wherein $R_1$ is selected from the group consisting of hydrogen, lower alkyl, or haloalkyl;

$R_2$ is selected from the group consisting of hydrogen or alkyl;

$R_3$ and $R_4$ are one or more members each independently chosen from the group consisting of hydrogen, alkyl, acyloxy, alkoxy, nitro, amino, acylamino, alkylamino, diakylamino, dialkylaminoalkyl, sulfamyl, alkythio, mercapto, hydroxy, hydroxyalkyl, alkylsulfonyl, halogen, cyano, carboxyl, carbalkoxy, carbamido, haloalkyl or cycloalkoxy;

$R_5$ is an alkylsulfonyl; and

M is selected from the group consisting of hydroxy, substituted lower alkoxy, amino, alkylamino, dialkylamino, N-morpholino, hydroxyalkylamino, polyhydroxyamino, dialkylaminoalkylamino, aminoalklyamino, and the group OMe, wherein Me is a cation.

2. A method according to claim 1 wherein $R_3$ and $R_4$ are selected from hydrogen, alkyl, acyloxy, alkoxy, halogen, haloalkyl or cycloalkoxy.

3. A method according to claim 2 wherein $R_1$ is hydrogen.

4. A method according to claim 1 wherein M is hydroxy or methoxy.

5. The method according to claim 1 wherein said cells are colonic polyp cells.

6. The method according to claim 1 wherein said cells are precancerous lesion cells of the breast.

7. The method according to claim 1 wherein said cells are precancerous lesion cells of the skin.

8. A method for inhibiting growth of neoplastic cells, comprising exposing said cells, in the absence of sulindac, to a growth inhibiting effective amount of a compound of the formula B:

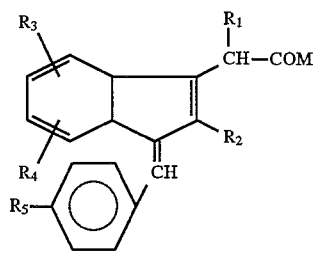

wherein $R_1$ is selected from the group consisting of hydrogen, lower alkyl, or haloalkyl;

$R_2$ is selected from the group consisting of hydrogen or alkyl;

$R_3$ and $R_4$ are one or more members each independently chosen from the group consisting of hydrogen, alkyl, acyloxy, alkoxy, nitro, amino, acylamino, alkylamino, diakylamino, dialkylaminoalkyl, sulfamyl, alkythio, mercapto, hydroxy, hydroxyalkyl, alkylsulfonyl, halogen, cyano, carboxyl, carbalkoxy, carbamido, haloalkyl or cycloalkoxy;

$R_5$ is an alkylsulfonyl; and

M is selected from the group consisting of hydroxy, substituted lower alkoxy, amino, alkylamino, dialkylamino, N-morpholino, hydroxyalkylamino, polyhydroxyamino, dialkylaminoalkylamino, aminoalklyamino, and the group OMe, wherein Me is a cation.

9. A method according to claim 8 wherein $R_3$ and $R_4$ are selected from hydrogen, alkyl, acyloxy, alkoxy, halogen, haloalkyl or cycloalkoxy.

10. A method according to claim 9 wherein $R_1$ is hydrogen.

11. A method according to claim 8 wherein M is hydroxy or methoxy.

* * * * *